US010406091B2

(12) United States Patent
Jenkins et al.

(10) Patent No.: US 10,406,091 B2
(45) Date of Patent: Sep. 10, 2019

(54) SKIN ANTI-AGEING COMPOSITION

(71) Applicant: Conopco, Inc., Englewood Cliffs, NJ (US)

(72) Inventors: Gail Jenkins, Bedfordshire (GB); Silvina Beatriz Lotito, Bedfordshire (GB); Jennifer Elizabeth Pople, Bedfordshire (GB); Linda Jane Wainwright, Bedfordshire (GB)

(73) Assignee: Conopco, Inc., Englewood Cliffs, NJ (US)

( * ) Notice: Subject to any disclaimer, the term of this patent is extended or adjusted under 35 U.S.C. 154(b) by 399 days.

(21) Appl. No.: 14/361,756

(22) PCT Filed: Nov. 27, 2012

(86) PCT No.: PCT/EP2012/073697
§ 371 (c)(1),
(2) Date: May 30, 2014

(87) PCT Pub. No.: WO2013/083431
PCT Pub. Date: Jun. 13, 2013

(65) Prior Publication Data
US 2014/0295010 A1    Oct. 2, 2014

(30) Foreign Application Priority Data

Dec. 6, 2011 (EP) .................................. 11192180

(51) Int. Cl.
*A61K 36/00* (2006.01)
*A61K 8/63* (2006.01)
*A61K 8/49* (2006.01)
*A61Q 19/08* (2006.01)
*A61K 9/00* (2006.01)

(52) U.S. Cl.
CPC ............. *A61K 8/63* (2013.01); *A61K 8/498* (2013.01); *A61K 9/0014* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 6,579,543 B1 | 6/2003 | McClung | |
| 6,605,296 B1 | 8/2003 | Stuckler | |
| 2002/0115618 A1 | 8/2002 | Rosenbloom | |
| 2002/0173472 A1 | 11/2002 | Pezzuto et al. | |
| 2002/0183400 A1 | 12/2002 | Baldo et al. | |
| 2005/0019426 A1 | 1/2005 | Wirth et al. | |
| 2005/0048008 A1 | 3/2005 | Gupta | |
| 2005/0095305 A1* | 5/2005 | Arias | A61K 8/97 424/732 |
| 2005/0186171 A1 | 8/2005 | Winick | |
| 2006/0035846 A1 | 2/2006 | Duranton et al. | |
| 2006/0040000 A1 | 2/2006 | Gokaraju et al. | |
| 2006/0078530 A1 | 4/2006 | Liu | |
| 2006/0110415 A1 | 5/2006 | Gupta | |
| 2006/0229265 A1 | 10/2006 | Milburn et al. | |
| 2006/0251608 A1 | 11/2006 | Wachsberg et al. | |
| 2007/0048246 A1 | 3/2007 | Sovak et al. | |
| 2007/0190209 A1 | 8/2007 | Sinnott | |
| 2007/0225360 A1 | 9/2007 | Pinnell et al. | |
| 2008/0057088 A1 | 3/2008 | Blass et al. | |
| 2008/0070883 A1 | 3/2008 | Nagpal | |
| 2008/0248129 A1 | 10/2008 | Bartunek et al. | |
| 2008/0254135 A1 | 10/2008 | Heuer et al. | |
| 2008/0262081 A1 | 10/2008 | Raederstorff et al. | |
| 2009/0012183 A1 | 1/2009 | Draijer et al. | |
| 2009/0028895 A1 | 1/2009 | Smith | |
| 2009/0047309 A1 | 2/2009 | Maes et al. | |
| 2009/0068132 A1 | 3/2009 | Bratescu et al. | |
| 2009/0130139 A1 | 5/2009 | Mekideche | |
| 2009/0263367 A1 | 10/2009 | Foley | |
| 2009/0324705 A1 | 12/2009 | Vikhrieva | |
| 2010/0015072 A1 | 1/2010 | Polla et al. | |
| 2010/0015262 A1 | 1/2010 | Goralczyk et al. | |
| 2010/0076035 A1 | 3/2010 | Carter et al. | |
| 2010/0099640 A1 | 4/2010 | Geuns et al. | |
| 2010/0215781 A1 | 8/2010 | Opheim | |
| 2010/0233128 A1 | 9/2010 | Panaseko | |
| 2010/0310615 A1 | 12/2010 | Vercauteren | |

(Continued)

FOREIGN PATENT DOCUMENTS

| | | |
|---|---|---|
| CN | 1260170 | 7/2000 |
| CN | 1351487 | 5/2002 |

(Continued)

OTHER PUBLICATIONS

Celik et al, Inhibitory effects of dietary flavonoids on purified hepatic NADH-cytochrome b5 reductase: Structure-activity relationships, Chemico-Biological Interactions, Apr. 19, 2012, 103-109, 197, TR.
Chang, Molecular Endocrinology, Liver X Receptor is a Therapeutic Target for Photoagine and Chronological Skin Aging, Sep. 11, 2008, 1-29, ., US.
Kratzer et al, Synthetic LXR agonist attenuates plaque formation in apoE-/- mice without inducing liver steatosis and hypertriglyceridemia, Journal of Lipid Research, 2009, 312-326, 50, AT.
Lindahl et al, Flavonoids as phospholipase A2 inhibitors: Importance of their structure for selective inhibition of Group II Phosphilipas A2, Inflammation, 1997, 347-356, vol. 21 No. 3, SE.
Park et al, Flavonoids inhibit histamine release and expression of proinflammatory cytokines in mast cells, Archives of Pharmacal Research, Oct. 6, 2008, 1303-1311, vol. 31 No. 10, KR.
International Search Report, PCT/EP2012/073697, dated Apr. 10, 2013, 4 pp.

(Continued)

Primary Examiner — Terry A McKelvey
Assistant Examiner — Randall Winston
(74) Attorney, Agent, or Firm — Greenberg Traurig, LLP

(57) ABSTRACT

The invention relates to a skin anti-ageing composition. In particular a skin anti-ageing composition comprising myricetin or glycoside thereof, and at least one LXR alpha agonist. By skin ageing is meant the appearance or manifestation of any one or more of wrinkles or sagging, poor skin barrier such as dryness, scalp itch, or uneven skin tone such as age spots.

4 Claims, 2 Drawing Sheets

(56) References Cited

U.S. PATENT DOCUMENTS

| | | |
|---|---|---|
| 2010/0323042 A1 | 12/2010 | Collins et al. |
| 2011/0009496 A1 | 1/2011 | Lunsmann et al. |
| 2011/0129546 A1 | 1/2011 | Umbert Mill |

FOREIGN PATENT DOCUMENTS

| | | |
|---|---|---|
| CN | 1731978 | 2/2006 |
| EP | 1327438 A1 | 7/2003 |
| EP | 1493431 A2 | 1/2005 |
| EP | 1992322 | 11/2008 |
| EP | 2005941 | 12/2008 |
| EP | 2163238 | 3/2010 |
| ES | 2349966 | 1/2011 |
| FR | 2642305 A1 | 8/1990 |
| FR | 2938765 | 5/2010 |
| JP | 60120805 | 6/1985 |
| JP | 2001039849 A2 | 2/2001 |
| JP | 2007210956 A * | 8/2007 |
| JP | 2008239576 | 10/2008 |
| JP | 2010202617 | 9/2010 |
| WO | WO0069404 | 11/2000 |
| WO | WO03030857 | 4/2003 |
| WO | WO2004058213 | 7/2004 |
| WO | WO2004103376 A2 | 12/2004 |
| WO | WO2007029982 A1 | 3/2007 |
| WO | WO2007073765 | 7/2007 |
| WO | WO2007146023 | 12/2007 |
| WO | WO2008018106 | 2/2008 |
| WO | WO2008111796 A1 * | 9/2008 |
| WO | WO2008119070 | 10/2008 |
| WO | WO2009146365 | 12/2009 |
| WO | WO2010001096 | 1/2010 |
| WO | WO2010011331 | 1/2010 |
| WO | WO2010039529 | 4/2010 |
| WO | WO201090830 | 8/2010 |
| WO | WO2011018501 | 2/2011 |
| WO | WO2011055222 | 5/2011 |

OTHER PUBLICATIONS

European Search Report, EP 11 19 2180, dated Jun. 4, 2012, 3 pp.
Components of Chinese Hippophae Oil and its Application in Treatment of Chloasma, Hippophae, 2004, pp. 25-26 (no translation), vol. 17, No. 2, CN.

* cited by examiner

SKIN ANTI-AGEING COMPOSITION

The invention relates to a skin anti-ageing composition. In particular to a skin anti-ageing composition comprising myricetin or glycoside thereof, and at least one LXR alpha agonist. By skin ageing is meant the appearance or manifestation of any one or more of wrinkles or sagging, poor skin barrier such as dryness, scalp itch, or uneven skin tone such as age spots.

WO 2004/103376 (Unilever) describes a method of enhancing decorin and/or fibronectin synthesis in the skin of an animal or human which method comprises administering to said animal or human a nuclear liver X receptor (LXR) activating agent.

WO 03/030857 (Unilever) describes a topical or systemic composition for enhancing epidermal barrier, treating/preventing dry skin, soothing irritated, red and/or sensitive skin, boosting/maintaining involucrin levels or reducing the rate of ageing function of skin, the composition comprising LXR alpha agonists defined by two Markush structures and a dermatologically acceptable vehicle. Examples of suitable LXR alpha agonists are given as 4-androsten-3,16-dione, 4-androsten-3,16-dione, androst-4-ene-3,6,16-trione, 4-androsten-17beta-ol-3,16-dione acetate, 16-ketotestosterone, 3beta-acetoxypregna-5,16-dien-20-one, 3beta-acetoxypregna-5-en-20-one, 3beta-hydroxypregna-5,16-dien-20-one, 3beta-hydroxypregna-5-en-20-one, 5,16-dien-pregnane-3,20-diol, 4,16-dienpregna-3,20-dione, 4,17(20)-(cis)-pregnadien-3,16-dione, 4,17(20)-(trans)-pregnadien-3,16-dione, 4-pregnen-3,16,20-trione, 4,17(20)-pregnadien-11beta,21-diol-3-one, 5,17(20)-pregnadien-3,16-diol-diacetate, 5,17(20)-pregnadien-3,16-diol, 5-pregnen-3beta,16alpha,21-triol-20-one, 24-hydroxychol-4-en-3-one, cholesta-5,24-dien-3beta-ol, cis-guggal sterone and desmosterol.

US 2008/0070883 (Wyeth) discloses an anti-skin ageing composition comprising a therapeutically effective amount of an LXR modulator, optionally including a retinoic acid receptor (RAR) such as all-trans retinoic acid.

Chang et al (Molecular Endocrinology, doi:10.1210/me.2008-0232 (11 Sep. 2008)) discloses that LXR's are expressed in skin and that signalling is down-regulated in cell-based models of photoageing. A synthetic LXR ligand was observed to inhibit expression of cytokines and metalloproteinases in-vitro and induced expression of differentiation markers, ceramide biosynthesis enzymes, lipid synthesis and transport genes in keratinocytes.

There is an on-going need for improved anti-ageing compositions.

SUMMARY OF THE INVENTION

In a first aspect of the invention, a skin anti-ageing composition, preferably a topical or oral composition, is provided, wherein the composition comprises myricetin or glycoside thereof, and at least one LXR alpha agonist.

In a second aspect of the invention, a skin anti-ageing composition, preferably a topical or oral composition, is provided, wherein the composition comprises myricetin or glycoside thereof, and at least one LXR alpha agonist wherein the bioavailable amounts of the combination of myricetin or glycoside thereof, and the at least one LXR alpha agonist reduce the level of IL-8 in an enzyme-linked immunosorbent assay below that of either myricetin or glycoside thereof, or the at least one LXR alpha agonist.

In a third aspect of the invention, a cosmetic method for treating or preventing skin ageing is provided, the method comprising the step of topically applying or imbibing a composition according to the first or second aspects of the invention.

SUMMARY OF THE FIGURES

The invention is illustrated with reference to

DETAILED DESCRIPTION OF THE INVENTION

Figure 1:
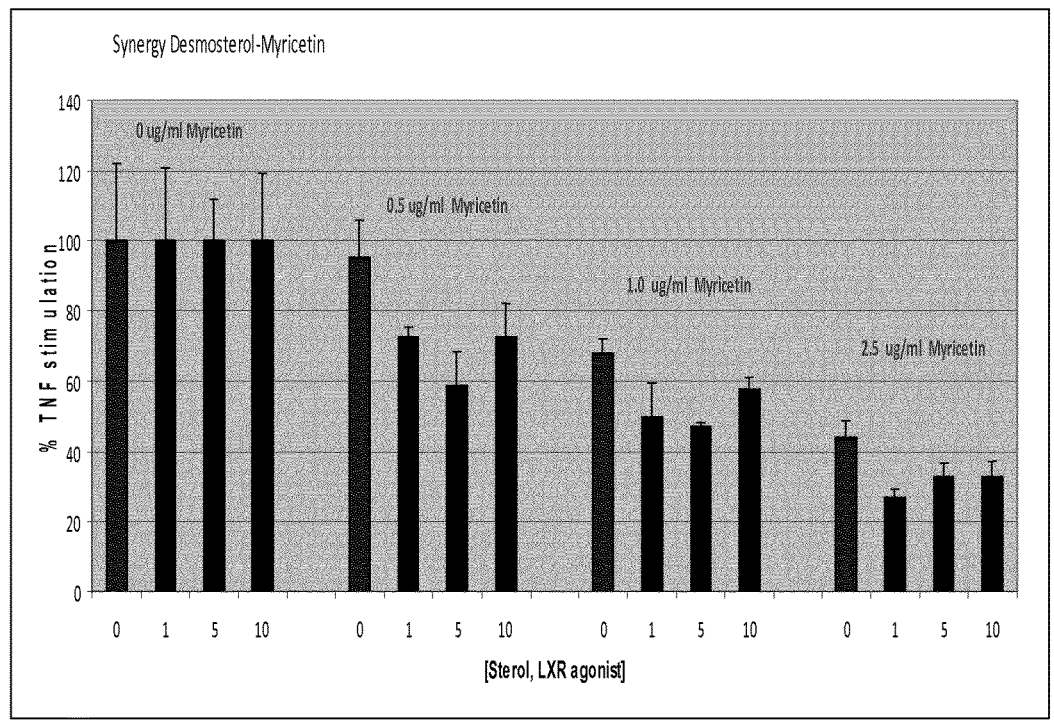
FIG. 1 which shows interleukin 8 (IL-8) response (pg per µg protein) for primary epidermal keratinocytes inflammatory challenged with 10 ng/ml TNF alpha pre-treated with 1-10 µM desmosterol, 0.5-2.5 µg/ml myricetin (1.57 to 18 µM) or both expressed as % of control (in the absence of myricetin) for each sterol concentration (controls are taken as 100%)

The inventors have observed a synergistic effect on down-regulation of interleukin 8 (IL-8) in epidermal keratinocytes treated with a combination of myricetin or glycoside thereof, and at least one LXR alpha agonist. IL-8 is a major mediator of the inflammatory response. Cutaneous cells should be expected to benefit from direct exposure to antioxidant and/or anti-inflammatory treatment (Thornfeldt, J. Cosmet. Dermatol. 7, 1, 78-82 (2008)). Visible skin ageing can be reduced and/or prevented by daily use of cosmeceuticals containing antioxidant and/or anti-inflammatory active components, coupled with a diet rich in antioxidant and/or anti-inflammatory foods (Perricone, The Wrinkle Cure. New York: Warner Books: 13-16, 48, 49 and 54-56 (2000)). LXR alpha agonists may be determined according to the reporter gene assay described in WO 03/030857 A1 (Unilever).

Thus a skin anti-ageing composition, preferably a topical or oral composition, is provided, wherein the composition comprises myricetin or glycoside thereof, and at least one LXR alpha agonist.

A skin anti-ageing composition, preferably a topical or oral composition, is also provided, wherein the composition comprises myricetin or glycoside thereof, and at least one LXR alpha agonist, wherein the bioavailable amounts of the combination of myricetin or glycoside thereof, and the at least one LXR alpha agonist reduce the level of IL-8 in an enzyme-linked immunosorbent assay below that of either myricetin or glycoside thereof, or the at least one LXR alpha agonist.

Myricetin and its glycosides may be provided in the form of an aqueous extract of red grapes, crowberries, cranberries, bilberries, aerial parts of *Abelmoschus moschatus* Myricetin, bayberries, bog wortleberries, black and red currants, black grapes, cabbage, onions, chilli peppers, rutabagas, sweet potato leaves, parsley, fennel, sow thistle, carob, green and black tea, and berry and grape wines.

Myricetin is a SirT1 agonist. SirT1 is also known as sirtuin and means silent mating type information regulation 2 homolog. A SirT1 agonist may be assayed using a kit from Sigma which is based on a two-step enzymatic reaction. The first step is deacetylation by SirT1 of a substrate that contains an acetylated lysine side chain. The second step is the cleavage of the deacetylated substrate by a developing solution and the release of a highly fluorescent group. The measured fluorescence is directly proportional to the deacetylation activity of the enzyme in the sample.

Thus it is thought that the aforementioned synergy is achieved by up-regulation activation of both the LXR alpha and SirT1 receptor proteins.

The LXR alpha agonist is preferably selected from the group consisting of stigmasterol, desmosterol, brassicasterol, 4,17(20)-(cis)-pregnadien-3,16-dione, 4,17(20)-(trans)-pregnadien-3,16-dione, guggal sterone, non-aqueous extract of *Boswellia serrata*, non-aqueous extract of Dragon's blood resin (*Daemorgos draco*), non-aqueous extract of Damar gum (exudate of Damar tree), non-aqueous extract of Breuzihno resin, non-aqueous extract of plantain, ursolic acid, non-aqueous extract of witch hazel, 22R-hydroxy cholesterol, N-(2,2,2-trifluoroethyl)-N-[4-[2,2,2-trifluoro-1-hydroxy-1-trifluoromethyl)ethyl]phenyl]-benzenesulfonamide, 4-androsten-3,16-dione, 4-androsten-3,16-dione, androst-4-ene-3,6,16-trione, 4-androsten-17-R-ol-3,16-dione acetate, 16-ketotestosterone, 3β-acetoxypregna-5,16-dien-20-one, 3β-acetoxypregna-5-en-20-one, 3β-hydroxypregna-5,16-dien-20-one, 3β-hydroxypregna-5-en-20-one, 5,16-dien-pregnane-3,20-diol, 4,16-dienpregna-3,20-dione, 4-pregnen-3,16,20-trione, 4,17 (20)-pregnadien-11β,21-diol-3-one, 5,17(20)-pregnadien-3,16-diol-diacetate, 5,17 (20)-pregnadien-3,16-diol, 5-pregnen-3β,16α,21-triol-20-one, 24-hydroxychol-4-en-3-one, cholesta-5,24-dien-3β-ol, non-aqueous extract of *Commiphora mokul*, non-aqueous extract of apple peel, non-aqueous extract of allspice, non-aqueous extract of clove, non-aqueous extract of *Lamium albim*, and mixtures thereof, more preferably from the group consisting of stigmasterol, desmosterol, brassicasterol, and mixtures thereof. Stigmasterol may be provided in the form of plant fats or oils of soybean, calabar bean, and rape seed, and as organic solvent extracts of *Ophiopogon japonicus* (Mai men dong) and American *Ginseng*. Brassicasterol may be obtained from rapeseed oil, coconut oil, corn-germ oil, linseed oil, peanut oil, soy oil, almonds, cashew nuts, lindseeds, and certain crabs. Sources of desmosterol are oysters, clams, scallops, red algae, and certain crabs such as Alaskan king crabs.

Topical compositions according to the invention typically comprise 0.0001-10, preferably 0.001-5, most preferably 0.001-2.5% w/w myricetin or glycoside thereof. The corresponding ranges for the LXR alpha agonist is typically 0.0001-10, preferably 0.001-5, most preferably 0.001-2.5% w/w. These levels of myricetin or glycoside thereof of the invention and LXR alpha agonist ensure that the in-vitro levels in the following examples are reached.

Any commercially acceptable and conventional vehicles may be used in the topical compositions of the invention, acting as diluents, dispersants and/or carriers for the aforementioned agonists and for any other optional but often preferred ingredients. Therefore a cosmetically acceptable vehicle suitable for use in this invention may be aqueous-based, anhydrous or an emulsion, a water-in-oil or oil-in-water emulsion being generally preferred. If the use of water is desired, water typically makes up the balance of the composition, and can make up from about 5 to 99, preferably 5 to 95, and most preferably from 30 to 70% w/w of the topical composition, including all ranges subsumed therein.

In addition to water, organic solvents may be optionally included to act as carriers or to assist carriers within the compositions of the present invention. Illustrative and non-limiting examples of the types of organic solvents suitable for use in the present invention include alkanols like ethyl and isopropyl alcohol, mixtures thereof or the like.

Other optional additives suitable for use include ester oils like isopropyl myristate, cetyl myristate, 2-octyldodecyl myristate, avocado oil, almond oil, olive oil, neopentylglycol dicaprate, mixtures thereof or the like. Typically, such ester oils assist in emulsifying the composition of this invention, and an effective amount is often used to yield a stable, and most preferably, water-in-oil emulsion.

Emollients may also be used, if desired, as carriers within the composition of the present invention. Alcohols like 1-hexadecanol (i.e. cetyl alcohol) are often desired as are the emollients generally classified as silicone oils and synthetic esters. Silicone oils suitable for use include cyclic or linear polydimethylsiloxanes containing from 3 to 9, preferably from 4 to 5, silicon atoms. Non-volatile silicone oils useful as an emollient material in the inventive composition described herein include polyalkyl siloxanes, polyalkylaryl siloxanes and polyether siloxane copolymers. The essentially non-volatile polyalkyl siloxanes useful herein include, for example, polydimethylsiloxanes.

Ester emollients that may optionally be used are:
(1) Alkenyl or alkyl esters of fatty acids having 10 to 20 carbon atoms. Examples thereof include isoarachidyl neopentanoate, isononyl isonanonoate, oleyl myristate, oleyl stearate and oleyl oleate.
(2) Ether-esters such as fatty acid esters of ethoxylated fatty alcohols.
(3) Polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory.
(4) Wax esters such as beeswax, spermaceti, stearyl stearate and arachidyl behenate.
(5) Sterols esters, of which cholesterol fatty acid esters are examples.

Emollients, when used, typically make up from about 0.1 to 50% w/w of the composition.

Fatty acids having from 10 to 30 carbon atoms may also be included as acceptable carriers within the composition of the present invention. Illustrative examples of such fatty acids include pelargonic, lauric, myristic, palmitic, stearic, isostearic, oleic, linoleic, arachidic, behenic or erucic acid, and mixtures thereof. Compounds that are believed to enhance skin penetration, like dimethyl sulfoxide, may also be used as an optional carrier.

Humectants of the polyhydric alcohol type may also be employed in the compositions of this invention. The humectant often aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.2 to 25, and preferably from about 0.5 to about 15% w/w of the composition including all ranges subsumed therein.

Thickeners may also be utilized as part of the acceptable carrier in the compositions of the present invention. Typical thickeners include cross-linked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, *sclerotium*, carrageenan, pectin and combinations of these gums. Amounts of the thickener may range from 0.0001 to 5, usually from 0.001 to 1, optimally from 0.01 to 0.5% w/w of the composition and including all ranges subsumed therein.

Collectively the water, solvents, silicones, esters, fatty acids, humectants and/or thickeners will constitute the acceptable carrier in amounts from 1 to 99.9, preferably from 80 to 99% w/w of the composition and including all ranges subsumed therein.

Surfactants may also be present in compositions of the present invention. Total concentration of the surfactant will range from 0.001 to 40, and preferably from 0.001 to 20, optimally from 0.01 to 5% w/w of the composition and including all ranges subsumed therein. The surfactant may be selected from the group consisting of anionic, nonionic, cationic and amphoteric actives. Particularly preferred nonionic surfactants are those with a C10-C20 fatty alcohol or acid hydrophobe condensed with from 2 to 100 moles of ethylene oxide or propylene oxide per mole of hydrophobe; mono- and di-fatty acid esters of ethylene glycol; fatty acid monoglyceride; sorbitan, mono- and di-C8-C20 fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, C8-C20 acyl isethionates, acyl glutamates, C8-C20 alkyl ether phosphates and combinations thereof.

Fragrances may be used in the composition of this invention. Illustrative non-limiting examples of the types of fragrance that may be used include those comprising terpenes and terpene derivatives like those described in Bauer, K., et al., Common Fragrance and Flavor Materials, VCH Publishers (1990). Illustrative yet non-limiting examples of the types of fragrances that may be used in this invention include myrcene, dihydromyrenol, citral, tagetone, cisgeranic acid, citronellic acid, mixtures thereof or the like. Preferably the amount of fragrance employed in the composition of this invention is in the range from 0.000001 to 10, more preferably 0.00001 to 5, most preferably 0.0001 to 2% w/w of the compound and including all ranges subsumed therein.

Various types of optional additional active ingredients may be used in the compositions of the present invention. Actives are defined as skin benefit agents other than emollients and other than ingredients that merely improve the physical characteristics of the composition. Although not limited to this category, general examples include talcs and silicas, as well as alpha-hydroxy acids, beta-hydroxy acids, zinc salts, and sunscreens.

Beta-hydroxy acids include salicylic acid, for example. Zinc pyrithione is an example of the zinc salts useful in the composition of the present invention.

Sunscreens include those materials commonly employed to block ultra-violet radiation. Illustrative compounds are the derivatives of para-aminobenzoic acid (PABA), cinnamate and salicylate. For example, avobenzophenone (Parsol 1789@) octyl methoxycinnamate and 2-hydroxy-4-methoxy benzophenone (also known as oxybenzone) can be used. Octyl methoxycinnamate and 2-hydroxy-4-methoxy benzophenone are commercially available under the trade marks, Parsol MCX™ and Benzophenone-3™, respectively. The exact amount of sunscreen employed in the compositions can vary depending upon the degree of protection desired from the sun's ultra-violet radiation. Additives that reflect or scatter the suns rays may also be employed. These additives include oxides like zinc oxide and titanium dioxide.

Many compositions, especially those containing water, should be protected against the growth of potentially harmful microorganisms. Anti-microbial compounds, such as triclosan, and preservatives are, therefore, typically necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from 0.1 to 2% w/w of the composition.

Still other optional ingredients that may be used with the composition of this invention include dioic acids (e.g. malonic acid and sebacic acid), antioxidants like vitamin E, retinoids, including retinoic acid, retinal, retinol and retinyl esters, conjugated linoleic acid, petroselinic acid and mixtures thereof, as well as any other conventional ingredients well known for wrinkle-reducing, anti-acne effects and reducing the impact of sebum.

When making a topical composition of the present invention, the desired ingredients are mixed in no particular order and usually at temperatures from about 70 to about 80° C. and under atmospheric pressure. The packaging for the topical composition of the invention can be a patch, bottle, tube, roll-ball applicator, propellant driven aerosol device, squeeze container or lidded jar.

A cosmetic method for treating or preventing skin ageing is also provided, the method comprising the step of topically applying or imbibing the composition of the invention.

More generally, use of a composition according to the invention is provided for treating or preventing skin ageing. Alternatively, a composition according to the invention is provided for use as a medicament. More specifically, a composition according to the invention is provided for use in treating or preventing skin ageing. In a further alternative, use of a composition according to the invention is provided for the manufacture of a medicament for treating or preventing skin ageing.

Oral compositions of the invention may take any suitable form, including, for example food products and nutritional supplements. The term "oral" means edible by a human. The format of the oral compositions may be capsules, pills, tablets, granules, solutions, suspensions or emulsions. Thus oral consumption may include beverages, bars and other liquid and solid forms such as tablets, pills, capsules and powders (which may contain crystalline material), as well as spreads, margarines, creams, sauces, dressings, mayonnaises, ice creams, fillings, confectionaries and cereals. Preparation of such formats is well known to the person skilled in the art.

The composition preferably comprises one or more additional components selected from the group consisting of antioxidants, flavouring agents, preservatives, emulsifiers and stabilisers.

Suitable antioxidants can be selected, although not exclusively, from the following list, either singularly or in combination: TBHQ, ascorbyl esters (e.g. ascorbyl palmitate), ascorbic acid, tocopherols, rosemary extract, fruit concentrates or extracts, black or green tea extract, propyl gallate, butylated hydroxyanisole (BHA), butylated hydroxytoluene (BHT), citric acid or esters, tocotrienols, polyphenols, phenolic compounds, other flavonoids and oxygen scavengers. Especially preferred additional antioxidants are vitamins C and E. Not only are these effective antioxidants but they also have been shown to give skin benefits when consumed. The amount of antioxidant may be added in a sufficient amount to prevent the composition from significantly oxidising over a typical shelf-life of at least 6 months. Clearly the amount of antioxidant will depend on the type and activity of the antioxidant used.

The addition of a flavouring may be unnecessary if the myricetin or glycoside thereof, or LXR alpha agonist of the claimed composition is provided by a flavoured substance such as a vegetable or fruit juice. Suitable flavouring agents may be natural or synthetic. Flavouring agents may be required to make the product more palatable for consumption.

Food grade phospholipid emulsifiers are preferred, such as lecithin. Phospholipid emulsifiers are oil soluble, but lecithin can be added to either phase prior to emulsification. Preferably it is added to the aqueous phase. Any emulsifier is preferably present in the composition in an amount of at least 0.01, preferably from 0.05 to 3, more preferably from 0.1 to 1% w/w.

The composition may comprise polyunsaturated fatty acids, such as an omega-3 fatty acid (i.e. an unsaturated carboxylic acid having from 12 to 26 carbon atoms). Preferred omega-3 fatty acids are those selected from docosahexaenoic acid (DHA), eicosapentaenoic acid (EPA) and mixtures thereof. Suitable polyunsaturated fatty acids may also be selected from oleic acid, linoleic acid, gammalinoleic acid, linolenic acid, arachidonic acid. The polyunsaturated fatty acid may be present as a component of a natural oil, such as a fish oil.

The composition may also comprise soy isoflavones (including genistein or daidzein in glycosylated and/or non-glycosylated form), typically in an amount of from 0.0001 to 0.1% w/w.

The inventive composition may also be sold in the form of a kit with a topical composition, the topical composition having the same skin anti-ageing benefits as the inventive composition. Thus such a kit comprising an oral and topical composition both for skin anti-ageing can, when in use, then act both from "inside" and "outside" the skin to provide the skin care benefit.

In one embodiment, the inventive composition is preferably water based, i.e. comprises at least 50, preferably at least 60, most preferably at least 70% w/w water. It may be either liquid or frozen. The product thus has the sensation of being a regular water-based product and can be consumed on a regular basis as part of a consumer's normal diet. For example it could replace a fruit juice normally consumed at breakfast time. The inventive composition is preferably packaged as a beverage, for example, in a container such as a carton or a bottle of coated paper or cardboard, glass or plastic. The container preferably has a volume of from 10 to 500 ml, such as from 20 to 100 ml.

In an alternative embodiment, the inventive composition is contained in a capsule, provided together with instructions informing the user of a proposed dosage regime. The capsule may be made of any suitable material well known in the art such as gelatin. The capsule is adapted to be swallowed by the consumer and typically one or two capsules will be taken from one to four times per day. Daily dosages for myricetin or glycoside thereof of the invention are 20 to 20 000 mg and for the LXR alpha agonist 0.15 to 20 000 mg.

Thus a cosmetic method for treating or preventing skin ageing is also provided, the method comprising administering the oral inventive composition on a daily basis in the form of at least one, preferably at least two, more preferably at least three, most preferably at least four equal or unequal servings.

Alternatively the inventive composition may be included as one component of a complex food product, for instance the composition may be present in solid or gelatinous form as a filling or layer within a bar or similar product. The composition may therefore be included in a wide range of everyday food stuffs, for instance in "health food" bars which could be eaten as an alternative to other snack foods.

Oral compositions may be made by preparing an aqueous phase and an oil phase. If an emulsifier is used, it is preferred that it is added to the aqueous phase. The oil phase and aqueous phase are then blended together to form an emulsion. In a preferred process, the oil is on a powdered carrier material to assist emulsion formation. The emulsion may then be packaged in a sealed container such as a metal, coated cardboard or plastics container. The container is then preferably sealed so as to give no headspace or a gas-filled (e.g. nitrogen or carbon dioxide) headspace which excludes oxygen. This assists still further in preventing oxidation. Alternatively the emulsion may be frozen and packaged and sold as a frozen consumer product.

EXAMPLES

Materials
Myricetin (Sigma Aldrich M6760)
IL-8 ELISA (R&D systems: Human CXCL8/IL8 DuoSet ELISA DY208)
Brassicasterol B4935 (Sigma Aldrich)
Desmosterol D6513 (Sigma Aldrich)
Stigmasterol S2424 (Sigma Aldrich)
Tumour necrosis factor alpha 11371843001 (Roche Applied Science)

Outline of Experimental Approach

An in-vitro model has been developed to investigate the impact of an inflammatory stimulus on epidmeral keratinocytes, in which:
a. Cells are grown in 24-well (2.0 cm$^2$) plates.
b. The cells are pre-treated with active ingredient of interest for 24 hours then challenged with an inflammatory stimulus, 10 ng/ml tumour necrosis factor alpha (TNFa) in addition to the active ingredient, for a further 24 hours.
c. Cell culture supernatant and cell lysates were harvested at 24 hours (t24) post-TNFa treatment.
d. All cell culture supernatant was assayed for IL-8 as a measure of inflammatory response and cell culture lysate was assayed for total protein (BCA), as a measure of cytotoxicity.

Culture of Epidermal Cells

Primary human epidermal keratinocyte cells were cultured and passaged in fully supplemented KGM-Gold media (Lonza) with 70 µM calcium added. Cells were routinely plated out in 24-well tissue culture dishes, at a seeding density of ~50,000 cells/well in 1 ml medium/well for 24 hours, and incubated at 37° C. in 5% $CO_2$.

Addition of Test Solutions

Test solutions were prepared in KGM-Gold media without supplemented hydrocortisone and antibiotic. Media was removed from the cells and test solutions were added for 24 hours. The epidermal keratinocytes were then stimulated with an inflammatory challenge for 24 hours using 10 ng/ml TNFa in the presence of the test solutions. The treated supernatant (cell culture supernatant) was removed and stored at −20° C. prior to IL-8 analysis.

The epidermal keratinocytes were washed with 1 ml of Dulbecco's phosphated buffer solution (PBS) and 250 µl of ice cold lysis buffer (1% NP-40, 0.1% sodium deoxycholate, 0.1% sodium dodecyl sulphate, 6 mM sodium chloride and 0.05 M Tris at pH 7.6) containing protease inhibitor cocktail (Roche, Complete™ mini tablets 1 836 170) was added. The lysates were clarified by scraping the samples with a 1 ml syringe plunger and passing through an Acrowell™ filter plate (Pall) using an Acroprep™ vacuum manifold (Pall) into a 96 well microwell plate (Sterilin). The clarified lysates were stored at −20° C. until total protein estimation.

The total protein concentration of each clarified cell lysate was measured using the Pierce BCA protein assay kit so that the response to effect of the test substances could be normalised to ug protein. A set of eight standard solutions ranging from 0 to 1200 µg/ml protein was prepared from the supplied 2 mg/ml bovine serum albumin (BSA) stock solution. 10 µl of standard or cell lysate was added to duplicate wells of a flat-bottomed 96-well plate. The reagent solution was prepared according to the kit instructions from 50 parts reagent A and 1 part reagent B. 200 µl of the final reagent was added to each well. The plate was mixed, covered and incubated at 37° C. for 30 minutes and absorbance read at 562 nm. A protein standard curve was constructed and used to determine the protein concentration of each cell lysate.

The IL-8 concentration of each cell culture supernatant was assayed using the DuoSet Human IL-8 ELISA assay (R&D Systems DY208) according to the manufacturer's instructions. The IL-8 capture antibody was bound to the microtitre plate (Greiner) overnight at room temperature in phosphate buffered saline and removed by washing three times was wash buffer (0.05% Tween 20 in PBS) on an automatic plate washer. The plate was blocked with 300 µl of 1% bovine serum albumin (BSA) in phosphate buffered saline for 1 hour at room temperature and washed 3 times in wash buffer. Seven IL-8 standards were prepared in reagent diluent (0.1% BSA, 0.05% Tween 20 in PBS) at concentrations ranging from 0 to 2000 µg/ml. 100 µl of cell culture supernatant or standard was added to duplicate wells and incubated at room temperature for 2 hours. The plate was washed 3 times with wash buffer before 100 µl of IL-8 detection antibody diluted in reagent diluent was added and incubated for 2 hours at room temperature. The plate was washed 3 times with wash buffer before 100 µl of diluted streptavidin HRP was added to each well and incubated in the dark for 20 minutes at room temperature. The plate was washed 3 times with wash buffer then 100 µl of TMB substrate solution (Sigma T0440) was added to each well and incubated until colour developed (approx 5-10 minutes). 50 µl of stop solution (2 M $H_2SO_4$) was applied to each well and the plate was read on a microplate spectrophotometer (Dynex MRX) at 450 nm. A standard curve was plotted of mean optical density versus IL-8 concentration and the line of best fit calculated by regression analysis. The unknown concentration of IL-8 protein in all of the samples was estimated from this.

Figure 2:
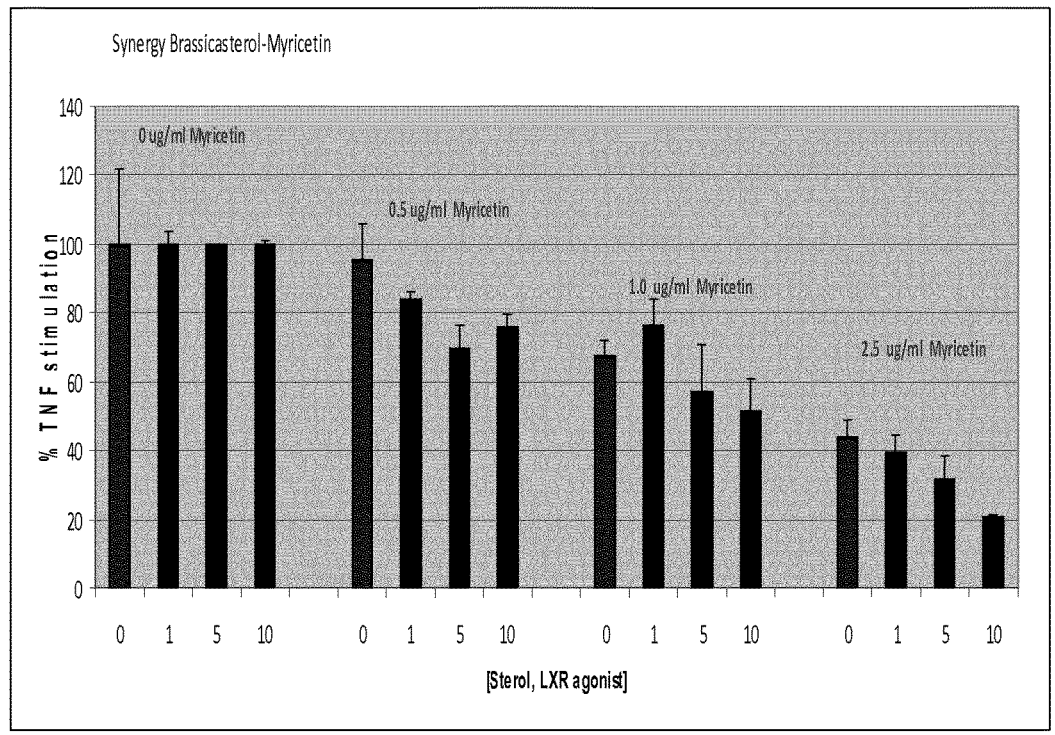
FIG. 2 which shows interleukin 8 (IL-8) response (pg per µg protein) for primary epidermal keratinocytes inflammatory challenged with 10 ng/ml TNF alpha pre-treated with 1-10 µM brassicasterol, 0.5-2.5 µg/ml myricetin (1.57 to 18 µM) or both expressed as % of control (in the absence of myricetin) for each sterol concentration (controls are taken as 100%)
Figure 3:
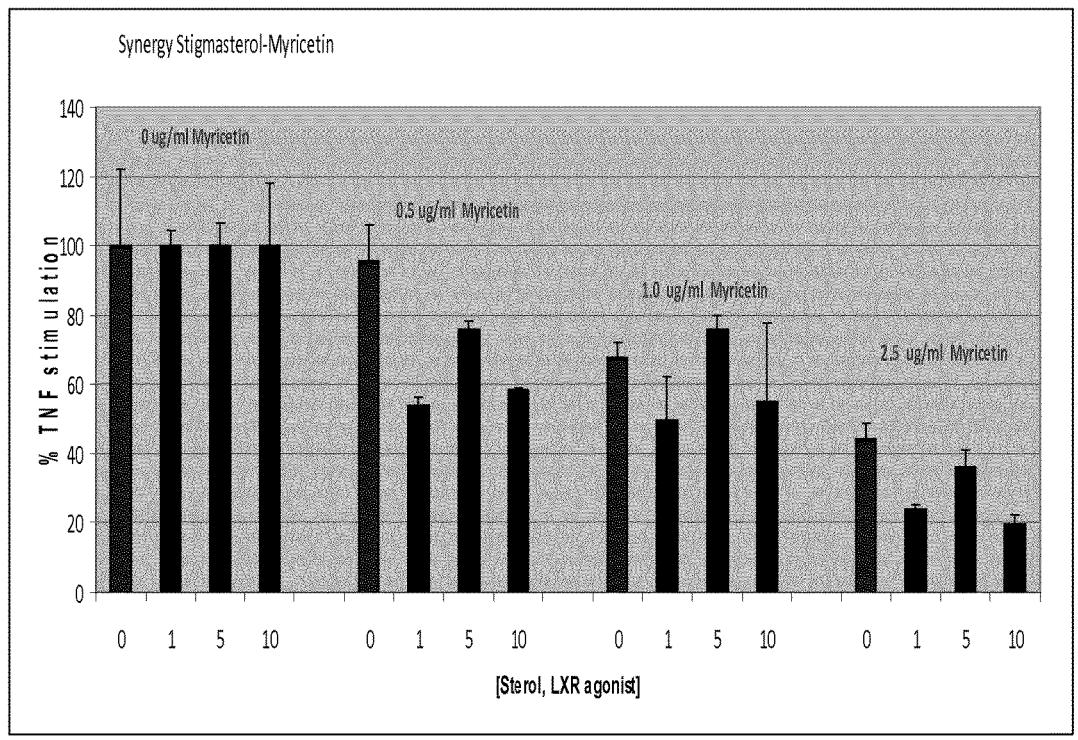
FIG. 3 which shows interleukin 8 (IL-8) response (pg per µg protein) for primary epidermal keratinocytes inflammatory challenged with 10 ng/ml TNF alpha pre-treated with 1-10 µM stigmasterol, 0.5-2.5 µg/ml myricetin (1.57 to 18 µM) or both expressed as % of control (in the absence of myricetin) for each sterol concentration (controls are taken as 100%).

The results appear in tables 1 to 3 and FIGS. 1 to 3. The figures express the results as % of control (in the absence of myricetin) for each sterol concentration (controls are taken as 100%).

TABLE 1

IL-8 (pg/µg protein) for desmosterol, myricetin and combinations thereof. T test at 95% confidence limits.

|  | IL-8 (pg/µg protein) | IL-8 (pg/µg protein) | T test |
| --- | --- | --- | --- |
| TNFalpha | 4.0497414 | 0.8797335 |  |
| DMSO or ethanol control | 0.3587931 | 0.0527452 |  |
| Desmosterol 1 uM | 4.7558499 | 1.0012139 |  |
| Desmosterol 5 uM | 4.7985769 | 0.5605329 |  |
| Desmosterol 10 uM | 4.7114028 | 0.9060584 |  |
| Myricetin 0.5 ug/ml | 3.8741852 | 0.4271353 |  |
| Myricetin 0.5 ug/ml + Desmosterol 1 uM | 3.4521108 | 0.1363409 | 0.1572826 |
| Myricetin 0.5 ug/ml + Desmosterol 5 uM | 2.826234 | 0.4590822 | 0.0709444 |
| Myricetin 0.5 ug/ml + Desmosterol 10 uM | 3.4138757 | 0.4487625 | 0.2018053 |
| Myricetin 1 ug/ml | 2.7408774 | 0.179451 |  |
| Myricetin 1 ug/ml + Desmosterol 1 uM | 2.3754461 | 0.4563104 | 0.2012128 |
| Myricetin 1 ug/ml + Desmosterol 5 uM | 2.2707824 | 0.0394201 | 0.0343045 |
| Myricetin 1 ug/ml + Desmosterol 10 uM | 2.7273204 | 0.1334971 | 0.4697487 |
| Myricetin 2.5 ug/ml | 1.7838739 | 0.1879159 |  |
| Myricetin 2.5 ug/ml Desmosterol 1 uM | 1.2971961 | 0.0892864 | 0.0402474 |
| Myricetin 2.5 ug/ml Desmosterol 5 uM | 1.5865165 | 0.1664348 | 0.1909688 |
| Myricetin 2.5 ug/ml Desmosterol 10 uM | 1.5572565 | 0.2001374 | 0.1817006 |

With reference to FIG. 1, desmosterol showed a synergistic anti-inflammatory effect with myricetin at all dosage combinations tested. There was a greater reduction in IL-8 release for combinations of these actives compared to either single ingredient alone. The synergistic effect for myricetin and desmosterol did not increase with increasing levels of the phytosterol, suggesting subtle changes to the activity of myricetin or glycoside thereof of the invention and LXR alpha in combination provided the most beneficial anti-inflammatory effect.

TABLE 2

IL-8 (pg/µg protein) for brassicasterol, myricetin and combinations thereof. T test at 95% confidence limits.

|  | IL-8 (pg/µg protein) | IL-8 (pg/µg protein) | T test |
| --- | --- | --- | --- |
| TNFalpha | 4.0497414 | 0.8797335 |  |
| DMSO or ethanol control | 0.3587931 | 0.0527452 |  |
| Brassicasterol 1 uM | 3.3939471 | 0.1311337 |  |
| Brassicasterol 5 uM | 4.4476201 | 0.0032139 |  |
| Brassicasterol 10 uM | 4.8618474 | 0.036903 |  |
| Myricetin 0.5 ug/ml | 3.8741852 | 0.4271353 |  |
| Myricetin 0.5 ug/ml + Brassicasterol 1 uM | 2.8424524 | 0.0910956 | 0.0395546 |

TABLE 2-continued

IL-8 (pg/µg protein) for brassicasterol, myricetin and combinations thereof. T test at 95% confidence limits.

| | IL-8 (pg/µg protein) | IL-8 (pg/µg protein) | T test |
|---|---|---|---|
| Myricetin 0.5 ug/ml + Brassicasterol 5 uM | 3.1038465 | 0.2983037 | 0.0858278 |
| Myricetin 0.5 ug/ml + Brassicasterol 10 uM | 3.6883098 | 0.1740866 | 0.3131128 |
| Myricetin 1 ug/ml | 2.7408774 | 0.179451 | |
| Myricetin 1 ug/ml + Brassicasterol 1 uM | 2.5811565 | 0.2736887 | 0.2807049 |
| Myricetin 1 ug/ml + Brassicasterol 5 uM | 2.5332252 | 0.607833 | 0.3443202 |
| Myricetin 1 ug/ml + Brassicasterol 10 uM | 2.5161945 | 0.4577259 | 0.2921733 |
| Myricetin 2.5 ug/ml | 1.7838739 | 0.1879159 | |
| Myricetin 2.5 ug/ml Brassicasterol 1 uM | 1.3424159 | 0.1590128 | 0.0633045 |
| Myricetin 2.5 ug/ml Brassicasterol 5 uM | 1.4216946 | 0.2955419 | 0.1405644 |
| Myricetin 2.5 ug/ml Brassicasterol 10 uM | 1.0010825 | 0.0300362 | 0.0141509 |

Turning now to FIG. 2, brassicasterol at the higher doses tested (5 and 10 µM) showed an improved synergistic anti-inflammatory effect in combination with myricetin. The result which showed no significant synergistic anti-inflammatory effect is due to experimental variation apparent in cellular assays.

TABLE 3

IL-8 (pg/µg protein) for stigmasterol, myricetin and combinations thereof. T test at 95% confidence limits.

| | IL-8 (pg/µg protein) | IL-8 (pg/µg protein) | T test |
|---|---|---|---|
| TNFalpha | 4.0497414 | 0.8797335 | |
| DMSO or ethanol control | 0.3587931 | 0.0527452 | |
| Stigmasterol 1 uM | 4.6381083 | 0.1980214 | |
| Stigmasterol 5 uM | 3.8699613 | 0.2502556 | |
| Stigmasterol 10 uM | 4.9639763 | 0.9006794 | |
| Myricetin 0.5 ug/ml | 3.8741852 | 0.4271353 | |
| Myricetin 0.5 ug/ml + Stigmasterol 1 uM | 2.5063064 | 0.0963097 | 0.0238018 |
| Myricetin 0.5 ug/ml + Stigmasterol 5 uM | 2.9428325 | 0.091038 | 0.0473 |
| Myricetin 0.5 ug/ml + Stigmasterol 10 uM | 2.9118143 | 0.0079439 | 0.0430042 |
| Myricetin 1 ug/ml | 2.7408774 | 0.179451 | |
| Myricetin 1 ug/ml + Stigmasterol 1 uM | 2.3079856 | 0.5764087 | 0.2086327 |
| Myricetin 1 ug/ml + Stigmasterol 5 uM | 2.9324501 | 0.1542361 | 0.185382 |
| Myricetin 1 ug/ml + Stigmasterol 10 uM | 2.7329682 | 1.1132478 | 0.4964931 |
| Myricetin 2.5 ug/ml | 1.7838739 | 0.1879159 | |
| Myricetin 2.5 ug/ml Stigmasterol 1 uM | 1.1148972 | 0.0410232 | 0.0194674 |
| Myricetin 2.5 ug/ml Stigmasterol 5 uM | 1.4052803 | 0.1910934 | 0.0919059 |
| Myricetin 2.5 ug/ml Stigmasterol 10 uM | 0.9660847 | 0.1524734 | 0.0205507 |

According to FIG. 3, stigmasterol at 1 µM, in combination with myricetin showed the largest synergistic reduction in IL-8 release of any of the phytosterols tested. Generally increasing the amount of stigmasterol in the assay did not necessarily increase the synergistic anti-inflammatory effect suggesting subtle changes to the activity of myricetin or glycoside thereof of the invention and LXR activity were more beneficial in terms of an anti-inflammatory effect for this combination. The result which showed no significant synergistic anti-inflammatory effect is due to experimental variation apparent in cellular assays.

The invention claimed is:

1. A skin anti-ageing composition comprising:
   a) myricetin or a glycoside of myricetin, in an amount from 0.0001 to 10% w/w;
   b) at least one LXR alpha agonist, in an amount from 0.0001 to 10% w/w;
   wherein
      the amount of the myricetin and the amount of the at least one LXR alpha agonist in combination or
      the amount of the glycoside of myricetin and the amount of the at least one LXR alpha agonist in combination
   exhibits a synergistic anti-inflammatory effect, wherein the synergistic anti-inflammatory effect is detectable by a reduction in IL-8 levels in an enzyme-linked immunosorbent assay, wherein the reduction in IL-8 levels indicative of the synergistic anti-inflammatory effect is greater than either
      the reduction in IL-8 levels due to the amount of myricetin alone plus the reduction in IL-8 levels due to the amount of the at least one LXR alpha agonist alone or
      the reduction in IL-8 levels due to the amount of the glycoside of myricetin alone plus the reduction in IL-8 levels due to the amount of the at least one LXR alpha agonist alone; and
   c) a cosmetically acceptable vehicle or an orally acceptable vehicle;
   wherein the LXR alpha agonist is selected from the group consisting of stigmasterol, desmosterol, brassicasterol and mixtures thereof.

2. The composition according to claim 1 for use as a medicament.

3. The composition according to claim 1 for use in treating or reducing skin ageing.

4. The composition according to claim 1, wherein the composition is an oral composition.

* * * * *